(12) United States Patent
Guo et al.

(10) Patent No.: US 12,329,859 B2
(45) Date of Patent: *Jun. 17, 2025

(54) BIOERODIBLE DRUG DELIVERY DEVICES

(71) Applicant: EyePoint Pharmaceuticals, Inc., Watertown, MA (US)

(72) Inventors: Hong Guo, Watertown, MA (US); Jianbing Chen, Watertown, MA (US)

(73) Assignee: EyePoint Pharmaceuticals, Inc., Watertown, MA (US)

( * ) Notice: Subject to any disclaimer, the term of this patent is extended or adjusted under 35 U.S.C. 154(b) by 346 days.

This patent is subject to a terminal disclaimer.

(21) Appl. No.: 17/697,084

(22) Filed: Mar. 17, 2022

(65) Prior Publication Data
US 2022/0202724 A1 Jun. 30, 2022

Related U.S. Application Data

(62) Division of application No. 16/006,395, filed on Jun. 12, 2018, now Pat. No. 11,298,323.

(60) Provisional application No. 62/518,739, filed on Jun. 13, 2017.

(51) Int. Cl.
*A61K 9/28* (2006.01)
*A61K 9/20* (2006.01)

(52) U.S. Cl.
CPC .............. *A61K 9/284* (2013.01); *A61K 9/204* (2013.01); *A61K 9/2072* (2013.01)

(58) Field of Classification Search
CPC ...... A61K 9/284; A61K 9/204; A61K 9/2072; A61K 9/70; A61K 9/0051; A61K 9/0092; A61K 31/58
See application file for complete search history.

(56) References Cited

U.S. PATENT DOCUMENTS

| | | | |
|---|---|---|---|
| 5,902,598 | A | 5/1999 | Chen et al. |
| 2004/0115268 | A1 | 6/2004 | Ashton et al. |
| 2005/0163844 | A1 | 7/2005 | Ashton |
| 2006/0067978 | A1 | 3/2006 | Heiler et al. |
| 2012/0202743 | A1 | 8/2012 | Cherif-Cheikh et al. |
| 2012/0207682 | A1 | 8/2012 | Ashton |
| 2012/0238993 | A1 | 9/2012 | Nazzaro et al. |
| 2013/0230564 | A1 | 9/2013 | Kleiner et al. |
| 2014/0154321 | A1 | 6/2014 | Ashton |
| 2014/0309610 | A1 | 10/2014 | Canham et al. |
| 2023/0098948 | A1* | 3/2023 | Guo ............ A61K 9/70 424/426 |

FOREIGN PATENT DOCUMENTS

| | | |
|---|---|---|
| WO | 2003051328 A1 | 6/2003 |
| WO | 2004066979 A2 | 8/2004 |
| WO | 2005051234 A2 | 6/2005 |
| WO | 2008036357 A2 | 3/2008 |

OTHER PUBLICATIONS

Makadia et al., Poly Lactic-co-Glycolic Acid (PLGA) as Biodegradable Controlled Drug Delivery Carrier. Polymers 2011, 3, 1377-1397. (Year: 2011).*
Deokule et al., "Evaluation of extended release brimonidine intravitreal device in normotensive rabbit eyes," Acta Ophthalmologica, 90(5):e344-e348 (2012).
Doppalapudi et al., "Biodegradable polymers—an overview," Polymers for Advanced Technologies, 25(5):427-435 (2014).
Extended European Search Report issued in EP 18818193.7 mailed Nov. 3, 2020.
International Search Report and Written Opinion mailed Sep. 4, 2018 in PCT/US18/37082.
Jessen et al., "Safety assessment of suboonjunctivally implanted devices containing latanoprost in Dutch-belted rabbits," Journal of Ocular Pharmacology and Therapeutics, 29(6):574-585 (2013).

* cited by examiner

*Primary Examiner* — Aradhana Sasan
(74) *Attorney, Agent, or Firm* — MEDLER FERRO WOODHOUSE & MILLS PLLC

(57) ABSTRACT

This invention relates to a bioerodible drug delivery device that can be implanted in a patient at or near an area in need of treatment. The bioerodible drug delivery device can be used to deliver a wide variety of different pharmaceutically active agents, and can do so at a controlled rate and over an extended period of time. The bioerodible drug delivery device includes a bioerodible polymeric outer housing with one or more delivery ports for delivering the pharmaceutically active agent(s) contained therein. The polymer used as the bioerodible polymeric outer housing is not substantially degraded during the dosing of the pharmaceutically active agent(s) in the bioerodible drug delivery device. The invention also provides methods of making the bioerodible drug delivery device and using it for the treatment of diseases and disorders.

17 Claims, 9 Drawing Sheets

BIOERODIBLE DRUG DELIVERY DEVICES

RELATED APPLICATIONS

The present application is a divisional of U.S. patent application Ser. No. 16/006,395 filed on Jun. 12, 2018, which claims benefit of Provisional Application No. 62/518,739, filed Jun. 13, 2017, the disclosures of each of which are incorporated fully herein by reference.

FIELD OF THE INVENTION

This invention relates to implantable bioerodible drug delivery devices for delivering a wide variety of pharmaceutically active agents. The invention also relates to methods of using such devices to treat patients in need of therapeutic relief, as well as methods of manufacturing such devices.

BACKGROUND OF THE INVENTION

Implantable drug delivery devices possess certain advantages over conventional dosing methods, such as oral administration or injection. For example, in conventional dosing methods, the concentration of a drug may vary considerably, reaching a maximum concentration (Cmax) shortly after administration and decreasing sharply afterwards. In order to maintain therapeutic levels, it may be necessary to administer the drug at high dosages, even though such dosages temporarily could result in high concentrations that are actually toxic to the patient. Subsequently, as drug is either metabolized in the body or is eliminated, the drug concentration may decrease to safe and therapeutic levels. When the drug level falls to sub-therapeutic levels, a subsequent dose may be administered and the cycle is thus repeated. Thus, a problem with conventional dosing is that, for certain types of drugs, a patient may be chronically exposed to undesirably high levels of the drug from the repeated dosing cycles required for treatment.

Implantable drug delivery devices can obviate many of these issues because implantation at or near the area in need of treatment reduces the need for high systemic concentrations of the drug in order to achieve therapeutic efficacy. However, achieving a constant dosing rate (so called zero-order release) can be challenging. In many systems, the release rate is time dependent, and the amount of drug released is proportional to the square root of time (or Fickian). For example, implantable devices that contain a drug that is dispersed within a matrix often do not exhibit zero-order release. While the drug near the outer surface of the matrix is released relatively easily, the drug located deeper within the core of the device must diffuse through the depleted matrix in order to be released. The net result is that the release rate slows down and Fickian release is common. With matrix systems, zero-order release is very difficult to achieve. The same principles apply to release from gels.

Another problem with many implantable drug delivery devices is that the devices may be constructed of non-biodegradable materials that permanently remain in a patient's body even after all of the drug has been administered. This may become problematic in many different situations. For example, when an implantable drug delivery device is to be implanted into an anatomical location with a small volume, the number of therapeutic treatments by implantation available to a patient may be limited due to the undesirable accumulation of the non-biodegradable portions of the implantable drug delivery device. This is particularly true when the implantable drug delivery device is implanted into an eye to treat an eye disease or disorder. Any non-biodegradable portion of the device that permanently remains in the eye presents a risk of interfering with the patient's vision. As another example, when an implantable drug delivery device is implanted into a joint to treat a musculoskeletal condition, non-biodegradable portions of the device that remain in the joint may interfere with the joint's full range of motion.

In view of all of the above, there remains a need in the art for improving the design and the method of preparing devices which provide controlled and sustained release of a drug to a patient to obtain a desired local or systemic physiological or pharmacological effect.

SUMMARY OF THE INVENTION

In one aspect, the invention provides an implantable bioerodible drug delivery device comprising a drug core that contains a pharmaceutically active agent. The device also has a bioerodible outer member that comprises a first bioerodible polymer that substantially surrounds the drug core. The first bioerodible polymer is not permeable to the pharmaceutically active agent following implantation of the device. The bioerodible outer member also has at least one delivery port comprising a second bioerodible polymer that is permeable to the pharmaceutically active agent following implantation of the device. The bioerodible outer member is configured to provide a substantially constant dosing rate of the pharmaceutically active agent over a predetermined period of treatment following implantation.

In another aspect, the invention provides a method of treating a patient. The method includes identifying an area of a patient in need of treatment and implanting a bioerodible drug delivery device in sufficient proximity to the area in need of treatment to provide therapeutic relief. The bioerodible drug delivery device comprises a drug core that contains a pharmaceutically active agent. The bioerodible drug delivery device also has a bioerodible outer member that substantially surrounds the drug core and that is impermeable to the pharmaceutically active agent following implantation of the device. The bioerodible outer member also has at least one delivery port comprising a second bioerodible polymer that is permeable to the pharmaceutically active agent following implantation of the device. The bioerodible outer member is configured to provide a substantially constant dosing rate of the pharmaceutically active agent over a predetermined period of treatment following implantation.

In yet another aspect, the invention provides a method of manufacturing an implantable bioerodible drug delivery device. The method includes the step of combining a pharmaceutically active agent with a solution comprising a first bioerodible polymer to form a granulate composition. The granulate composition is extruded and then coated with a second bioerodible polymer that is not permeable to the pharmaceutically active agent when the device is implanted. The coated extruded granulate composition is then dried and a third bioerodible polymer is applied to form one or more delivery ports. These delivery ports are permeable to the pharmaceutically active agent following implantation of the device.

DETAILED DESCRIPTION OF THE INVENTION

Figure 1:
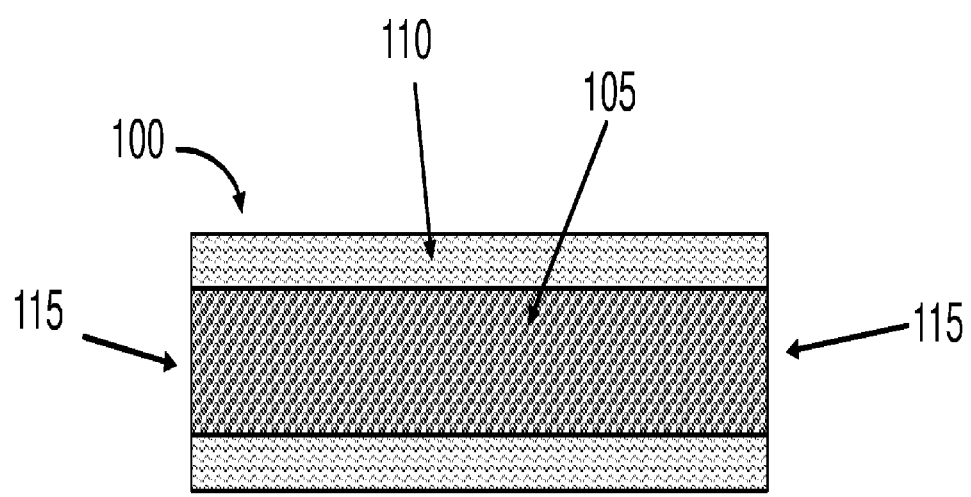
FIG. 1: An exemplary implantable bioerodible drug delivery device according to one embodiment of the invention in which the outer member comprises a single polymeric layer.

In one aspect, the invention provides an implantable bioerodible drug delivery device that is suitable for the controlled and sustained release of a pharmaceutically active agent in order to obtain local or systemic therapeutic relief for a patient in need thereof. As used herein, the terms "bioerodible" (and variants thereof) and "biodegradable" (and variants thereof) refer to the ability of a polymer or device, as the case may be, to be chemically broken down (e.g., via a hydrolysis reaction) or dissolved after the polymer or device has been implanted in vivo. An advantage of the present invention is that the drug delivery device does not need to be removed after the administration of the pharmaceutically active agent is complete. Rather, the drug delivery device may be left in vivo, where it slowly biodegrades over time to form harmless by-products that are eliminated by normal metabolic processes. Another advantage of the present invention is that the drug delivery device can be used to deliver pharmaceutically active agents at a constant rate over a predetermined period of time.

In general, the implantable bioerodible drug delivery devices of the invention include at least one drug core that comprises one or more pharmaceutically active agents. In many embodiments of the invention, the implantable bioerodible drug delivery devices of the invention contain exactly one drug core, although the invention expressly contemplates devices with two or more drug cores, which may contain the same or different pharmaceutically active agents. In certain embodiments, the drug core contains the pharmaceutically active agent without any additional additives. Typically, drug cores of this type are used when the pharmaceutically active agent has a relatively low solubility in vivo. However, if desired, the pharmaceutically active agent may be combined with a bioerodible polymer that acts as a bulking agent and/or controls the rate at which the pharmaceutically active agent will dissolve in vivo. Generally, the chosen bioerodible polymer should be chemically inert with respect to the pharmaceutically active agent, during manufacturing of the sustained release device, during subsequent storage, and after the sustained release device has been implanted into the area of a patient in need of treatment. Non-limiting examples of bioerodible polymers contemplated by the invention include polyvinyl alcohol (PVA) and poly(lactic-co-glycolic acid) (PLGA). In preferred embodiments, the bioerodible polymers constitute about 1 to about 5%, about 1 to about 10%, about 1 to about 20%, about 1 to about 25%, about 1 to about 30%, about 1 to about 35%, about 1-40%, about 1 to about 45%, or about 1 to about 50% of the drug core by weight.

In certain embodiments, a drug core may be formed by combining one or more pharmaceutically active agents in powder form with a solution that has a bioerodible polymer dissolved therein and mixing until the composition has the consistency of granulates and/or a paste. If desired, such compositions may be further processed by extruding them through a die. In certain embodiments, the extrudate has a generally cylindrical shape, although other shapes (e.g., cube, disk, etc.) are expressly contemplated by the invention. After extrusion, it is advantageous to dry the extrudate in order to remove the solvent of the bioerodible polymer solution. In certain embodiments, the extrudate is air dried at room temperature, although the invention also expressly contemplates drying with heat, preferably at temperatures that do not affect the stability of the one or more pharmaceutically active agents or any bioerodible polymers that have been added to the drug core.

The pharmaceutically active agents contemplated by the invention are not particularly limited and may include any pharmaceutically active agent that is sufficiently stable under manufacturing and storage conditions and that is compatible with the materials used to fabricate the implantable bioerodible drug delivery device.

The following exemplary classes of pharmaceutical agents may be incorporated into the devices of the present invention: anesthetics and pain killing agents such as lidocaine and related compounds and benzodiazepam and related compounds; anti-cancer agents such as 5-fluorouracil, adriamycin and related compounds; anti-fungal agents such as fluconazole and related compounds; anti-viral agents such as trisodium phosphomonoformate, trifluorothymidine, acyclovir, ganciclovir, DDI, DDC, and AZT; cell transport/mobility impending agents such as colchicine, vincristine, cytochalasin B, and related compounds; antiglaucoma drugs such as beta-blockers: timolol, betaxol, atenalol, etc.; immunological response modifiers such as muramyl dipeptide and related compounds; peptides and proteins such as cyclosporin, insulin, growth hormones, insulin related growth factor, heat shock proteins and related compounds, and carbonic anhydrase inhibitors.

In certain embodiments, the pharmaceutically active agent is an anti-inflammatory agent. For example, the pharmaceutically active agent may be a steroid or corticosteroid, non-limiting examples of which include fluocinolone acetonide, hydrocortisone, hydrocortisone acetate, triamcinolone acetonide, methylprednisolone, dexamethasone, medrysone, methylprednisolone, prednisolone 21-phosphate, prednisolone acetate, fluoromethalone and betamethasone. The invention also contemplates the use of non-steroidal anti-inflammatory drugs (NSAIDs). Non-limiting examples of NSAIDs include diclofenac, etodolac, fenoprofen, floctafenine, flurbiprofen, ibuprofen, indoprofen, ketoprofen, ketorolac, lomoxicam, morazone, naproxen, perisoxal, pirprofen, pranoprofen, suprofen, suxibuzone, tropesin, ximoprofen, zaltoprofen, zileuton, and zomepirac. The NSAIDs contemplated by the invention also include COX-2 inhibitors, examples of which include valdecoxib, rofecoxib, and celecoxib. In addition to the foregoing anti-inflammatory agents, the invention also expressly contemplates the use of analogs, derivatives, pharmaceutically acceptable salts, esters, prodrugs, codrugs, and protected forms thereof.

In addition to the above agents, other agents include neuroprotectants such as nimodipine and related compounds; tyrosine kinase inhibitors such as bosutinib and dasatinib, antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole, sulfisoxazole nitrofurazone and sodium propionate; antivirals, including idoxutidine; antiallergenics such as antazoline, methapyriline, chlorpheniramine, pyrilamine, and prophenpyridamine; fibrinolytic agents (e.g., tissue plasminogen activator, streptokinase and urokinase); deconges-tants such as phenylephrine, naphazoline, and tetrahydrozoline; miotics and anti-cholinesterase such as pilocarpine, eserine salicylate, carbachol, di-isopropyl fluorophosphate, phospholine iodine, and demecarium bromide; mydriatics such as atropine sulfate, cyclopentolate, homatropine, scopolamine, tropicamide, eucatropine, and hydroxyamphetamine; sympathomimetics such as epinephrine; and prodrugs such as those described in Design of Prodrugs, edited by Hans Bundgaard, Elsevier Scientific Publishing Co., Amsterdam, 1985. Once again, reference may be made to any standard pharmaceutical textbook such as Remington's Pharmaceutical Sciences for the identity of other agents.

In certain embodiments, the pharmaceutically active agent is an antibiotic agent. In some embodiments, the antibiotic agent may be administered as the sole pharmaceutically active agent in the implantable bioerodible drug delivery devices according to the invention. In other embodiments, however, antibiotic agents are co-administered with another pharmaceutically active agent. For example, in cases where an implantable biodegradable drug delivery device containing an anti-inflammatory agent is to be surgically implanted to treat a musculoskeletal disorder, an antibiotic agent may be co-administered to reduce the possibility of infection at the surgical wound. The administration of the antibiotic agent in such cases may be via a separate sustained delivery device that is co-implanted. Alternatively, the antibiotic agent may be combined with the anti-inflammatory agent, such that they are part of the same drug core. The type of antibiotic is not particularly limited, and may be any antibiotic with the requisite chemical stability to withstand the manufacturing process and subsequent storage conditions prior to use. Non-limiting examples of antibiotic compounds contemplated by the invention include aminoglycosides (e.g., amikacin, gentamicin, kanamycin, neomycin, netilmicin, tobramycin, paromomycin, streptomycin, spectinomycin), carbapenems (e.g., meropenem, imipenem, doripenem), cephalosporins (e.g., cefixime, cefdinir, cefditoren, cefoperazone, cefotaxime, cefepime, ceftobiprole), glycopeptides (teicoplanin, vancomycin, telavancin, dalbavancin, oritavancin), lincosamides (clindamycin, lincomycin), and macrolides (e.g, azithromycin, erythromycin).

In addition to the drug core, the implantable drug delivery devices according to the invention include a bioerodible outer member that houses the drug core. Typically, the bioerodible outer member comprises one or more bioerodible polymers that substantially cover or coat the drug core and is of an appropriate composition and sufficient thickness to retain its shape and to be impermeable to the pharmaceutically active agent in the drug core during the predetermined period of treatment. In general, the bioerodible polymer that is used to fabricate the bioerodible outer member is not limited, and may be any bioerodible polymer that has the requisite biocompatibility for use as an implant and impermeability during the predetermined period of treatment. Non-limiting examples of bioerodible polymers that are suitable for the implantable drug delivery devices of the invention include poly(lactic-co-glycolic acid), polylactic acid, poly-glycolic acid and polyvinyl alcohol and mixtures thereof. For a given implantable drug delivery device, bioerodible polymer, and desired predetermined period of treatment, the appropriate thicknesses that renders the bioerodible outer housing impermeable may be determined by diffusion cell studies carried out under sink conditions, as described herein. Useful wall thicknesses for the bioerodible outer housing may be, for example, in the range of about 40 μm to about 120 μm. In certain preferred embodiments, the bioerodible outer housing has a wall thickness that is at least about 40 μm, but less than or equal to about 100100 μm.

The implantable drug delivery devices of the invention may be equipped with one or more delivery ports to permit the delivery of the pharmaceutically active agent(s) in the drug core. It is to be understood that the size of the one or more delivery ports will govern the dosing rate, with larger delivery ports leading to a greater degree of solubilization per unit time and therefore a faster dosing rate. In certain implementations of the invention, a delivery port may be simply an aperture in the bioerodible outer member that permits the drug core to have direct contact with the bodily fluids of a patient after implantation. In such implementations, the direct contact between the drug core and bodily fluids will, over time, lead to the solubilization and release of the pharmaceutically active agent(s) of the drug core into the bodily fluids and surrounding tissue. Delivery ports of this type are particularly suitable in situations where the drug core has low solubility in the bodily fluids that contact the drug core after implantation. In such implementations, the size of the one or more apertures preferably remains essentially constant during the predetermined period of treatment, so as to facilitate a substantially constant dosing rate. In addition, a delivery port may be fabricated by creating an aperture in the bioerodible outer member and covering the aperture with a permeable bioerodible polymer. In such cases, the permeable bioerodible polymer may be used to regulate the rate of diffusion of the pharmaceutically active agent(s) of the drug core into the surrounding tissue following implantation. This may be achieved, for example, by choosing a permeable bioerodible polymer with a degradation rate that is sufficiently slow in vivo that the permeability is essentially constant during the predetermined period for treatment. In this way, one can achieve a constant dosing rate over the predetermined period of treatment (zero-order release kinetics), provided that the concentration of solubilized drug in the device remains constant during the predetermined period of treatment. In certain preferred embodiments, the bioerodible polymer layer on the delivery port has a varied thickness, which was adjustable by using different concentration of bioerodible polymer solution (0.05% to 10%) or by times of solution coating applied.

In preferred embodiments, the implantable bioerodible drug delivery devices of the invention release the pharmaceutically active agents at a substantially constant rate (i.e. zero-order drug release kinetics) over a predetermined period of time following an initial transient period after implantation. It is to be understood that in preferred embodiments of the invention, the initial transient period is much less than the predetermined period of time (e.g., less than 10%). Without wishing to be limited by theory, it is believed that the non-zero-order release kinetics during the initial transient period are caused by changes that occur as the implantable bioerodible drug delivery devices gradually reach steady state after implantation (e.g., wetting or diffusion phenomena). Diffusion cell studies under sink conditions may be conducted to determine the rate at which a particular pharmaceutically active agent is released through a given permeable bioerodible polymeric layer. Generally, such studies involve monitoring the diffusion of a pharmaceutically active agent between two compartments: a donor compartment and a receptor compartment. The concentration of drug in the receptor compartment is essentially zero when compared to the high concentration in the donor compartment. Under these conditions, the rate of drug release is given by:

$$\frac{Q}{t} = \frac{D \cdot K \cdot A \cdot DC}{h}$$

where Q is the amount of pharmaceutically active agent released, t is time, D is the diffusion coefficient, K is the partition coefficient, A is the surface area, DC is the difference in concentration of the pharmaceutically active agent across the permeable bioerodible polymeric layer, and h is the thickness of the permeable bioerodible polymeric layer.

Under sink conditions, if release from the donor side is very slow, the value DC is essentially constant and equal to the concentration of the donor compartment. The release rate therefore becomes dependent on the surface area (A), thickness (h), and diffusivity (D) of the bioerodible polymeric layer. In the construction of the devices of the present invention, the size (and therefore surface area) is mainly dependent on the size of the pharmaceutically active agent. Thus, the permeability of a given bioerodible polymer layer of interest may be obtained from the slopes of a Q versus time plot. The permeability, P, can be related to the diffusion coefficient D, by the equation:

$$P = \frac{K \cdot D}{h}$$

Once the permeability is established for the permeable bioerodible polymer layer of interest with regard to the diffusion of the pharmaceutically active agent therethrough, the appropriate device dimensions may be determined to achieve a desired dose and dosing rate. The device dimensions, such as diameter and length, can be adjusted together with the diffusion port surface area to tailor the release rates and released amount of the pharmaceutically active agent, as taught herein. It is to be understood that, in the implantable drug delivery devices of the invention that comprise a permeable bioerodible polymeric layer over the delivery apertures, the pharmaceutically active agent diffuses in the direction of lower chemical potential, i.e., toward the exterior surface of the device. At the exterior surface of the device, equilibrium is again established. A steady state flux of the effective agent will be established in accordance with Fick's Law of Diffusion, when equilibrium on both sides of a permeable bioerodible polymeric layer of a delivery aperture is reached. Under this condition, the drug concentration on both sides of the permeable bioerodible polymeric layer become constant with respect to time, but obviously are not the same. The rate of passage of the pharmaceutically active agent through the permeable bioerodible polymeric layer by diffusion is generally dependent on the solubility of the drug therein, as well as on the thickness of the layer. Accordingly, the selection of appropriate materials as well as the dimensions of the device (such as but not limited to, the thickness of the bioerodible polymer, the interior diameter of the device, the thickness of polymer capping the ends of the device, the dimensions of the delivery ports) and the active ingredient formulation all work together in concert to achieve the desired release rate of the active agent as well as ensure that all or substantially all of the active agent has been delivered to the patient from the delivery port(s) before the bioerodible polymer degrades to the level that exposes the drug core. Thus, the materials and the device dimensions and the active agent are carefully chosen to fabricate the device to achieve the contemplated and the desired predetermined period of treatment. Thus, for example, an implantable device may be designed to deliver a pain control drug for a short period of time (e.g., two weeks) at a high dose to bring therapeutic relief, while an implantable device of the same size may be used to deliver an anti-inflammatory agent for six months at a much lower dose.

The bioerodible outer member may be fabricated using different techniques in accordance with the invention. For example, in certain embodiments, the bioerodible outer member may be formed by dip-coating a drug core of the invention in a solution containing a bioerodible polymer, non-limiting examples of which include poly(lactic-co-glycolic acid), polylactic acid, poly-glycolic acid, polycaprolactone, and polyvinyl alcohol and mixtures thereof. Non-limiting examples of suitable solutions include those containing about 1 to about 20%, about 2 to about 18%, about 5 to about 15%, about 8 to about 12%, or about 10% w/w of a bioerodible polymer. If desired, a drug core may be dipped multiple times into a bioerodible polymer solution to increase the thickness of a bioerodible outer member. For example, a bioerodible outer member of a desired thickness may be formed around a drug core by repeated cycles of dipping the drug core into a solution containing a bioerodible polymer and air drying the polymer coating. In some embodiments, two or more different types of bioerodible polymers may be co-dissolved in a dip-coating solution. In the alternative, the invention also contemplates successive dip-coating processes in which the drug core is dipped into different polymer solutions. In such embodiments, the drug core may be dipped into each type of polymer solution once or multiple times, as needed, in order to achieve the requisite coating for the given application.

When the drug core is dip-coated to form an impermeable bioerodible outer member, it is often the case that the entire drug core is entirely covered with an impermeable bioerodible polymeric coating. To form delivery ports in such cases, it is advantageous to create corresponding openings in the impermeable bioerodible polymeric layer order for delivering the pharmaceutically active agent. If desired, one can use mechanical means to create the delivery ports, including puncturing, grinding, or cutting the impermeable bioerodible polymeric layer. In one non-limiting embodiment, a cylindrical drug core that is formed by extrusion and that is dip-coated in an impermeable bioerodible polymeric layer is cut transversally to create a delivery port as a cross-section that exposes the drug core. If desired, the exposed drug core may be coated with a bioerodible polymer that is permeable to the pharmaceutically active agent after implantation of the device to control the delivery rate of the pharmaceutically active agent. While the foregoing description relates to a cylindrical implantable bioerodible drug delivery device with one delivery port, it is to be understood that the invention also expressly contemplates devices with two or more delivery ports. For example, a cylindrical drug core formed by extrusion and dip-coated in an impermeable bioerodible polymeric layer may be cut transversally at both ends to form two delivery ports, which optionally may be coated with a permeable bioerodible polymer. If desired, the extruded drug core may be heat treated either before dip-coating, in between dip-coating steps, or after the completion of dip coating to drive off any solvents that may have been used in the manufacturing process. In general, the heat treatment is performed at a temperature that can safely drive off the solvent without causing undesirable degradation of the pharmaceutically active agent(s) or undesirable side reactions. In addition, a heat treatment step can be performed to alter the permeability or rate of in vivo degradation of the bioerodible polymers used to fabricate the implantable drug delivery devices of the invention. For example, when an implantable drug delivery device of the invention contains a polyvinyl alcohol layer, the permeability and the water solubility of the polyvinyl alcohol layer may be reduced by heat treating.

In other embodiments, the bioerodible outer member is a rigid article into which the drug core is inserted or deposited during manufacturing. For example, the bioerodible outer member may be a hollow rigid tubular member, into which the drug core is inserted or extruded. In one non-limiting embodiment, the drug core is initially a composition with a sufficiently low viscosity that it may be inserted or extruded into the rigid tubular bioerodible outer member by a plunger, pushrod, or the like. In some cases, the pharmaceutically active agent may be combined with a solvent (and optionally a bioerodible polymer) such that the viscosity of the initial drug core composition is sufficiently low that the composition may be poured, injected, or drawn into the tube by vacuum. In such cases, it may be advantageous to heat the device to drive off substantially all of the residual solvent prior to implantation.

In certain preferred embodiments, the outer diameter of the tubular bioerodible outer member is selected such that the implantable drug delivery device of the invention may be implanted into the eye of a patient using a needle with a gauge that is 25 or larger gauge (smaller needle) smaller. One aspect of the invention is the recognition that when the implantable drug delivery device is to be injected into the eye of a patient using such a needle, the wall of the tubular bioerodible outer member must be sufficiently thick to maintain both the structural integrity of the implantable drug delivery device during implantation and the desired zero-order release kinetics over a predetermined period of treatment. Thus, for example, when the tubular bioerodible outer member of such an implantable drug delivery device is made using poly(lactic-co-glycolic) acid (PLGA), useful wall thicknesses fall in the range of 40 to 80 µm. By using wall thicknesses in this range, the tubular PLGA bioerodible outer members will cause the implantable bioerodible drug delivery devices to exhibit substantially zero-order release kinetics after implantation into the eye, but the tubular PLGA bioerodible members still be completely degraded on a timescale on the order of the predetermined period of treatment. In this way, implantable drug delivery devices of this type may be sequentially implanted into a patient's eyes without accumulation of more than one spent device within the eye over the predetermined period of treatment.

In general, for ease of manufacturing, the implantable bioerodible drug delivery devices are preferably cylindrical in shape. However, other shapes are expressly contemplated, and regular shapes (e.g., cubes, disks, etc.) are particularly preferred. When the bioerodible drug delivery devices are cylindrical, the transverse cross-section (not illustrated) of such devices often will appear circular. While it is preferred to manufacture the implantable bioerodible drug delivery devices as cylinders with circular cross-sections, it is also within the scope of the present invention to manufacture such devices as cylinders with cross-sections of different shapes, such as ovals, ellipses, rectangles, including squares, triangles, as well as any other regular polygon or irregular shapes.

Turning now to the drawing figures, FIG. 1 shows a longitudinal cross-sectional view of implantable drug delivery device 100 according to one implementation of the invention. Device 100 comprises drug core 105 which contains one or more pharmaceutically active agents. The one or more pharmaceutically active agents optionally may be mixed with at least one bioerodible polymer that acts as a bulking agent and/or controls the rate of dissolution of the drug core in vivo. Device 100 further comprises bioerodible outer member 110, which is fabricated using a bioerodible polymer to create a housing that is substantially impermeable after implantation to the pharmaceutically active agent(s) contained in drug core 105, at least during the predetermined period of treatment. Device 100 also features two delivery ports 115 which are located at opposite ends of device 100. In this particular embodiment, the delivery ports 115 directly expose drug core 105 to the surrounding environment and it is expected that as drug core 105 is dissolved by bodily fluids after implantation of device 100, the pharmaceutically active agent(s) contained in drug core 105 will be emitted from delivery ports 115.

Figure 2:
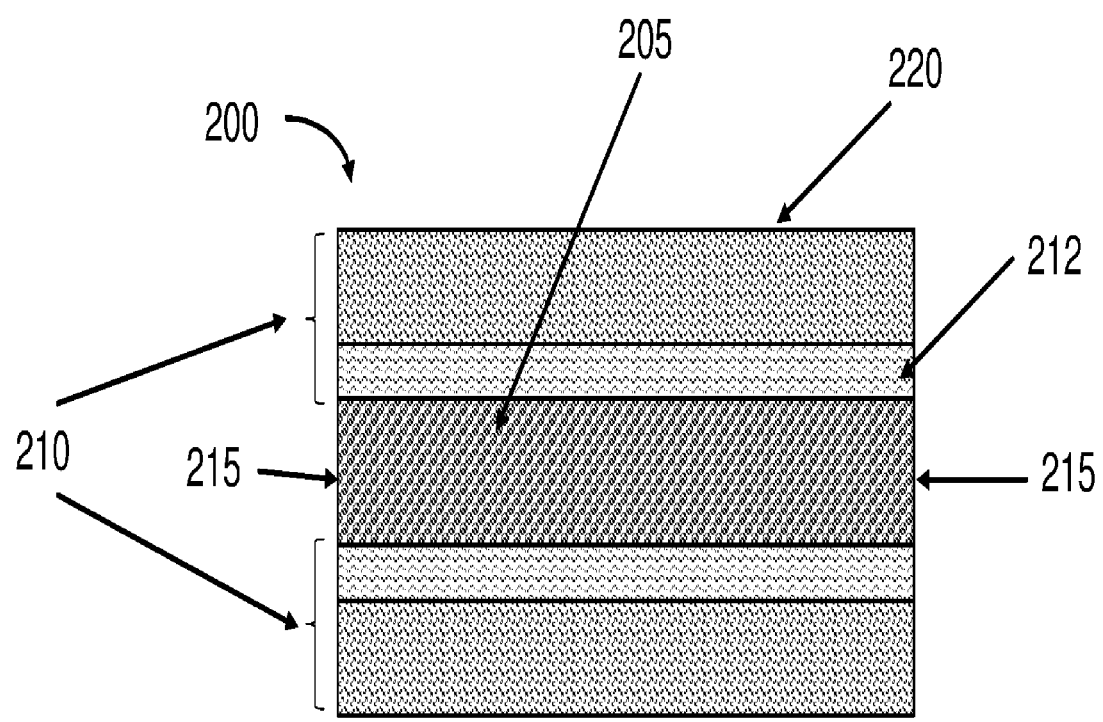
FIG. 2: An exemplary implantable bioerodible drug delivery device according to one embodiment of the invention in which the outer member comprises two different polymeric layers.

FIG. 2 shows a longitudinal cross-sectional view of implantable drug delivery device 200 according to another implementation of the invention. In FIG. 2, device 200 comprises a drug core 205 which contains one or more pharmaceutically active agents that optionally may be mixed with at least one bioerodible polymer that acts as a bulking agent and/or controls the rate of dissolution of the drug core in vivo. Device 200 further comprises bioerodible outer member 210, which is a multilayer structure comprised of a first bioerodible polymer layer 212 and a second bioerodible polymer layer 220. Although only two polymeric layers 212, 220 are depicted in FIG. 2, it is to be understood that the invention contemplates devices with bioerodible outer members that comprise three or more bioerodible polymer layers. Also, it should be noted that each polymeric layer of a bioerodible outer member 110, 210 independently may be comprised of a copolymer, (e.g., block copolymer, alternating copolymer, or random copolymer). Drug delivery device 200 further comprises two delivery ports 215, located at opposite ends of device 200. As in the case for FIG. 1, the delivery ports 215 in FIG. 2 directly expose drug core 205 to the surrounding environment. As drug core 205 is dissolved by bodily fluids after implantation of device 200, the pharmaceutically active agent(s) contained in drug core 205 will be emitted from delivery ports 215.

Figure 3A:
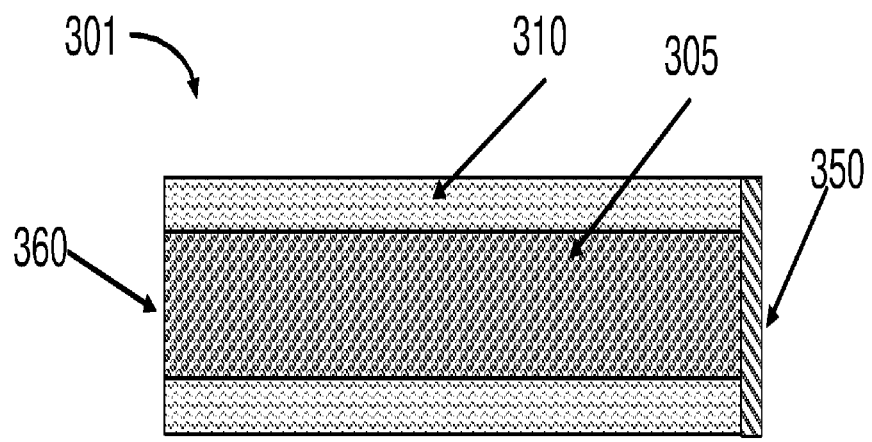
FIG. 3: (a) An exemplary implantable bioerodible drug delivery device according to one embodiment of the invention in which one end of the device is sealed with a polymer that that is impermeable to the pharmaceutically active agent in the drug core; (b) an exemplary implantable bioerodible drug delivery device according to one embodiment of the invention in which each end of the device comprises a delivery port comprising a polymeric layer that is permeable to the pharmaceutically active agent contained in the drug core.
Figure 3B:
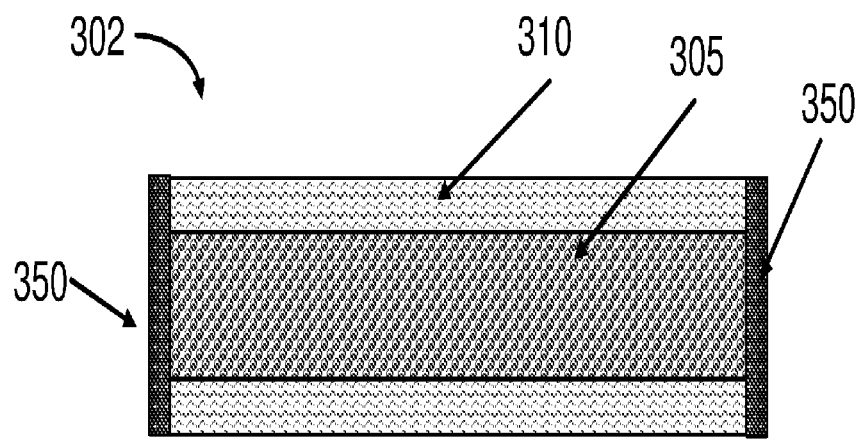

FIG. 3(a) shows a longitudinal cross-sectional view of implantable drug delivery device 301 according to another implementation of the invention. Device 301 includes drug core 305 which contains one or more pharmaceutically active agents that optionally may be mixed with at least one bioerodible polymer that acts as a bulking agent and/or controls the rate of dissolution of the drug core in vivo. Device 301 further comprises bioerodible outer member 310, which is fabricated using a bioerodible polymer to create a housing that substantially covers the pharmaceutically active agent(s) contained in drug core 305. The bioerodible polymer is substantially impermeable to the pharmaceutically active agent(s) contained in drug core 305, at least during the predetermined period of treatment. Device 301 features one delivery port 360 which directly exposes drug core 305 to the surrounding environment. As drug core 305 is dissolved by bodily fluids after implantation of device 301, the pharmaceutically active agent(s) contained in drug core 305 will be emitted from delivery port 360. At the other end of device 301, a bioerodible polymeric cap 350 that is impermeable to the pharmaceutically active agent(s) in drug core 305 prevents administration of such agent(s) from the end of the device where bioerodible polymeric cap 350 is located. While FIG. 3(a) shows the bioerodible polymeric cap 350 to be comprised of a polymer that is different from that of bioerodible outer member 310, it is to be understood that the bioerodible outer member and the bioerodible polymeric cap can be fabricated together as a single, monolithic unit, if desired. FIG. 3(b) shows a longitudinal cross-sectional view of implantable drug delivery device 302 according to another implementation of the invention. In FIG. 3(b), device 302 comprises drug core 305 which contains one or more pharmaceutically active agents that optionally may be mixed with at least one bioerodible polymer that acts as a bulking agent and/or controls the rate of dissolution of the drug core in vivo. Device 302 further comprises bioerodible outer member 310, which is fabricated using a bioerodible polymer to create a housing that substantially covers the pharmaceutically active agent(s) contained in drug core 305. The bioerodible polymer is substantially impermeable to the pharmaceutically active agent(s) contained in drug core 305, at least during the predetermined period of treatment. Device 302 features two delivery ports with permeable bioerodible polymer layers 350 that permit the pharmaceutically active agent(s) contained in drug core 305 to diffuse therethrough.

Figure 4A:
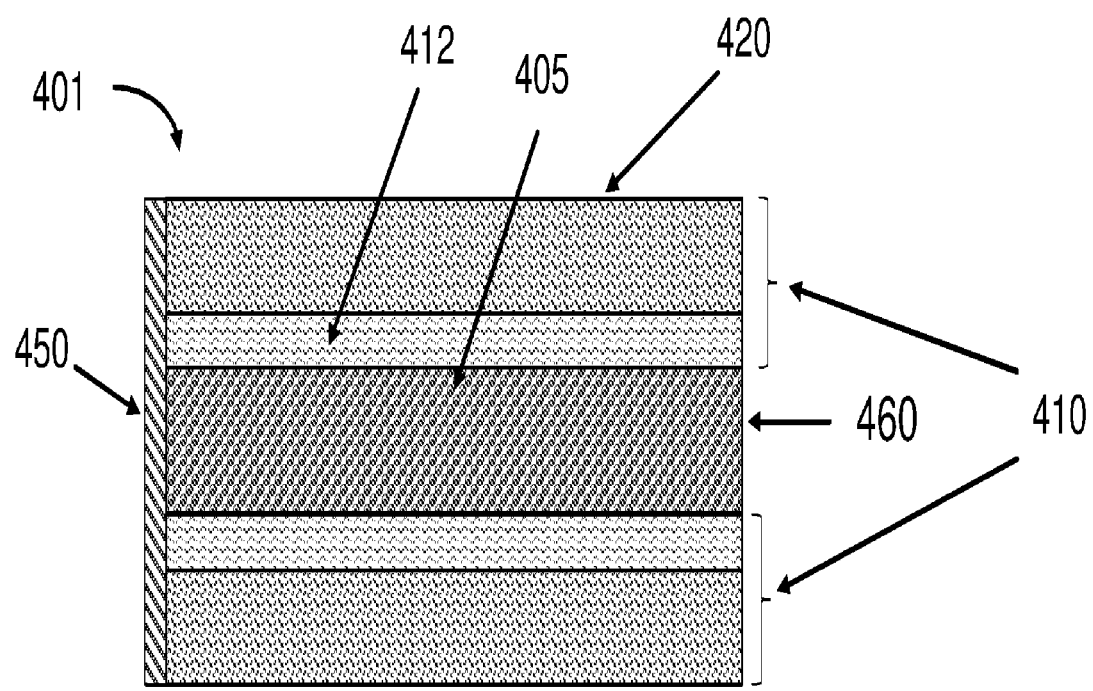
FIG. 4: (a) An exemplary implantable bioerodible drug delivery device according to one embodiment of the invention in which the bioerodible outer member comprises two polymeric layers and in which one end of the device is sealed with a polymer that is impermeable to the pharmaceutically active agent in the drug core; (b) an exemplary implantable bioerodible drug delivery device according to one embodiment of the invention in which the bioerodible outer member comprises two polymeric layers and each end of the device comprises a delivery port comprising a polymeric layer that is permeable to the pharmaceutically active agent contained in the drug core.

FIG. 4 shows additional embodiments of the invention. FIG. 4(a) provides a longitudinal cross-sectional view of implantable drug delivery device 401. Device 401 comprises a drug core 405 containing one or more pharmaceutically active agents that optionally may be mixed with at least one bioerodible polymer that acts as a bulking agent and/or controls the rate of dissolution of the drug core in vivo. Device 401 further comprises bioerodible outer member 410, which is a multilayer structure comprised of a first bioerodible polymer layer 412 and a second bioerodible polymer layer 420. Similar to the embodiment shown in FIG. 2, device 401 is not limited to a bioerodible outer member 410 with only two polymeric layers 412, 420. Rather, it is to be understood that three or more bioerodible polymer layers can be used to form bioerodible outer member 410. Also, it should be noted that each polymeric layer of a bioerodible outer member 410 may be comprised of a copolymer, (e.g., block copolymer, alternating copolymer, or random copolymer). Drug delivery device 401 further comprises a single delivery port 460 which directly exposes drug core 405 to the surrounding environment. Upon implantation, drug core 405 is gradually dissolved by bodily fluids and the pharmaceutically active agent(s) contained in drug core 405 will be emitted from delivery port 460. Bioerodible polymer cap 450, which is comprised of a polymer that is impermeable to the pharmaceutically active agent(s) of drug core 405 during the predetermined period of treatment, prevents release of the pharmaceutically active agent(s) from the end of device 401 opposite to delivery port 460. As in the case for FIG. 3(a), it is to be understood that the bioerodible outer member and the bioerodible polymer cap can be fabricated together as a unitary structure of the same material.

Figure 4B:
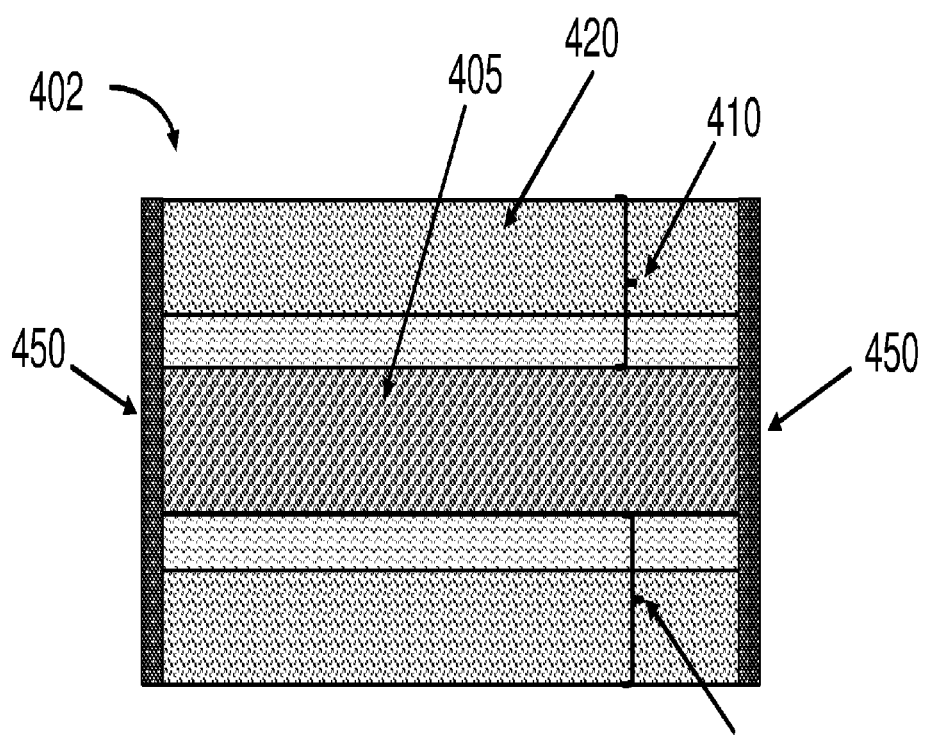

FIG. 4(b) provides a longitudinal cross-sectional view of implantable drug delivery device 402. As in the case device 401 in FIG. 4(a), device 402 in FIG. 4(b) includes drug core 405 which comprises one or more pharmaceutically active agents that optionally may be mixed with at least one bioerodible polymer that acts as a bulking agent and/or controls the rate of dissolution of the drug core in vivo. Device 402 further comprises bioerodible outer member 410, which is a multilayer structure comprised of a first bioerodible polymer layer 412 and a second bioerodible polymer layer 420. If desired, additional bioerodible polymers layers may be included, depending on the desired application and or predetermined period of treatment. Drug delivery device 402 further comprises two delivery ports which include permeable bioerodible polymer layers 450. Upon implantation, the bodily fluids of the patient permeate bioerodible polymeric layers 450 to solubilize drug core 405, thereby releasing the pharmaceutically active agent(s) contained therein.

Figure 5:
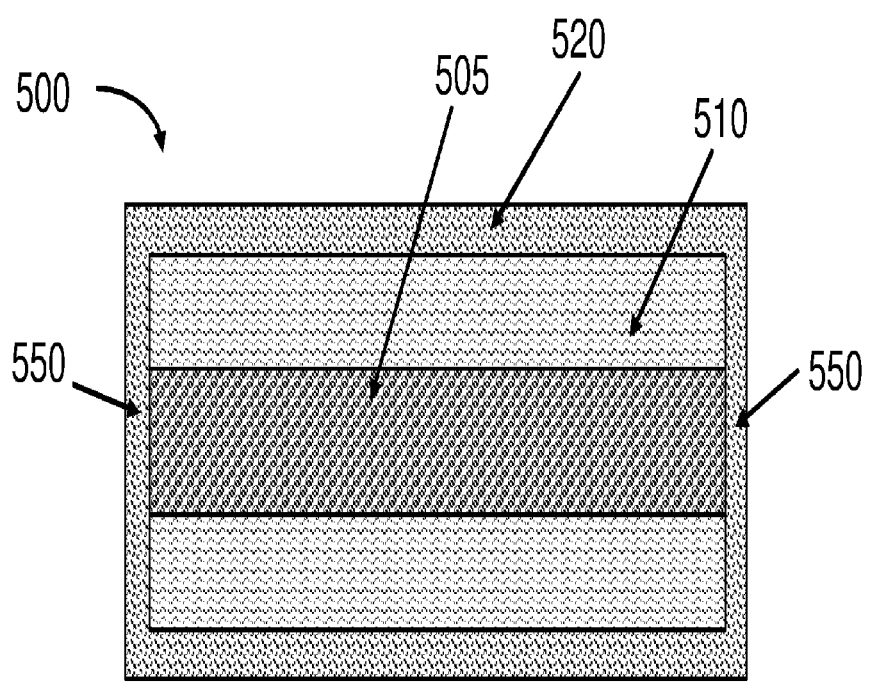
FIG. 5: An exemplary implantable drug delivery device according to one embodiment of the invention in which the outer member comprises two polymeric layers and the outermost polymer layer of the outer member also forms a part of the delivery port.

FIG. 5 provides a longitudinal cross-sectional view of an implantable drug delivery device 500 in accordance with another embodiment of the invention. Device 500 includes a drug core 505 comprising one or more pharmaceutically active agents that optionally may be mixed with at least one bioerodible polymer that acts as a bulking agent and/or controls the rate of dissolution of the drug core in vivo. Device 500 further comprises bioerodible outer member 510 which is fabricated using a bioerodible polymer that is impermeable to the pharmaceutically active agent(s) contained in drug core 505, at least during the predetermined period of treatment. Encapsulating the entire device is a bioerodible polymeric layer 520, which is permeable to the pharmaceutically active agent(s) contained in drug core 505. Upon implantation, drug core 505 is gradually dissolved by bodily fluids and the pharmaceutically active agent(s) contained in drug core 505 diffuse through the end regions 550.

Figure 6:
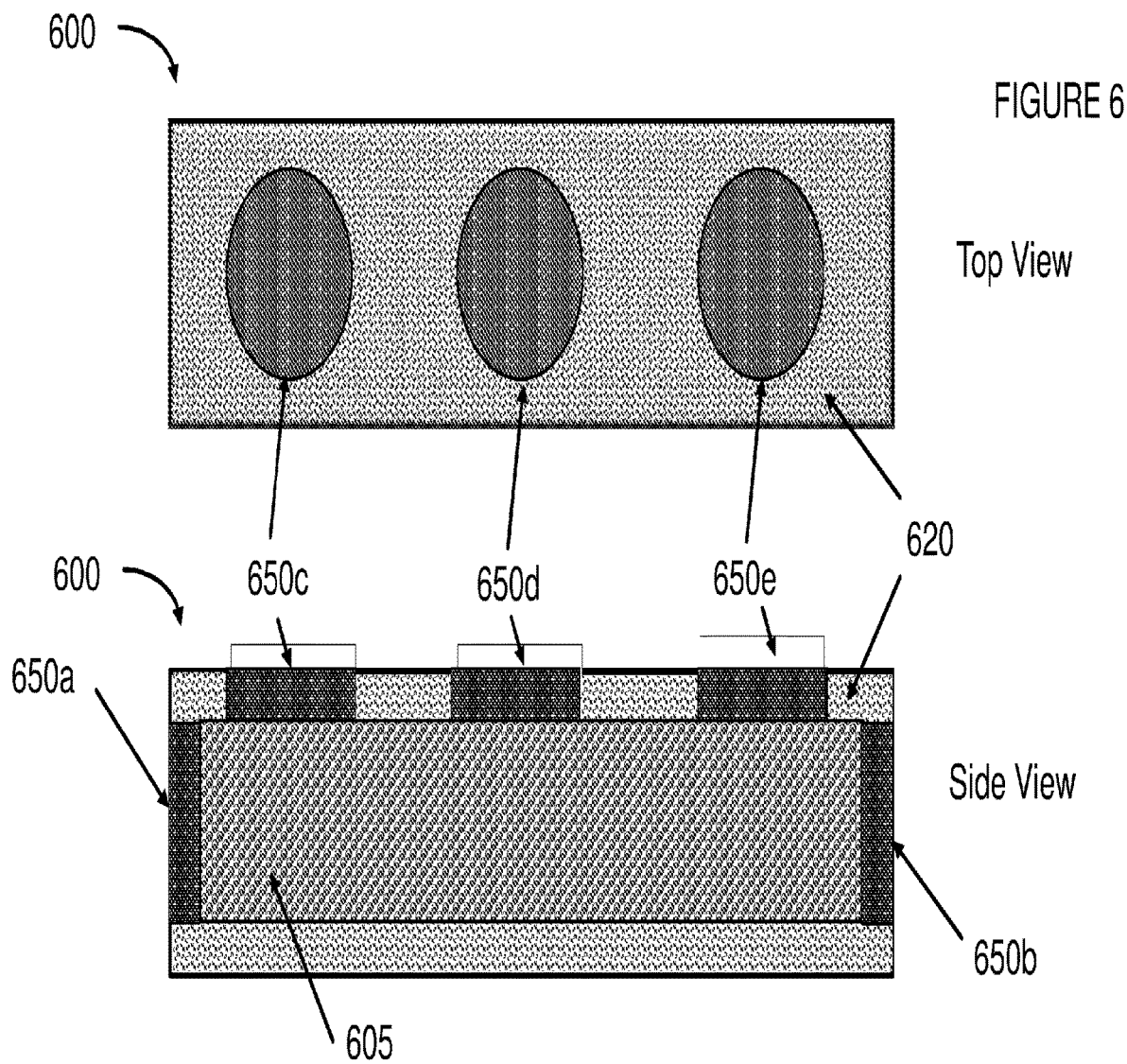
FIG. 6: An exemplary implantable drug delivery device according to one embodiment of the invention in which the outer member comprises a plurality of delivery ports.

FIG. 6 provides a top view and a longitudinal cross-sectional view of an implantable drug delivery device 600 in accordance with another embodiment of the invention. In FIG. 6, a drug delivery device 600 includes drug core 605 comprising one or more pharmaceutically active agents that optionally may be mixed with at least one bioerodible polymer that acts as a bulking agent and/or controls the rate of dissolution of the drug core in vivo. Device 600 further comprises bioerodible outer member 620, which is fabricated using a bioerodible polymer to create a housing that substantially covers the pharmaceutically active agent(s) contained in drug core 605. The bioerodible polymer is impermeable to the pharmaceutically active agent(s) in drug core 605, at least during the predetermined period of treatment. As shown in FIG. 6, device 600 features two delivery ports (650*a*, 650*b*) at each end of the device, with additional delivery ports (650*c*, 650*d*, and 650*e*) that are disposed along the length of device 600. It is expected that as drug core 605 is dissolved by bodily fluids after implantation of device 600, the pharmaceutically active agent(s) contained in drug core 605 will be emitted from delivery ports 650*a-e*. Thus, the presence of additional delivery ports is particularly useful when faster delivery of the pharmaceutically active agent(s) is desired after implantation of device 600. In certain embodiments, it is advantageous for ease of manufacturing and handling to have additional delivery ports 650*c*, 650*d*, and 650*e* located on the same side of device 600. For example, additional delivery ports 650*c*, 650*d*, and 650*e* may be arranged collinearly in the longitudinal direction along one side of device 600. This configuration is advantageous because it permits device 600 to be anchored or affixed to a body part via the longitudinal side of the device opposite to that of additional delivery ports 650*c*, 650*d*, and 650*e*, without affecting the dosing rate. In other embodiments, the additional delivery ports 650*c*, 650*d*, and 650*e* are not on the same side of device 600, which can result in a more spatially isotropic dosing profile. It is to be understood, however, that the number of delivery ports, the shapes of the delivery ports, and the specific locations of the delivery ports in FIG. 6 are merely illustrative not meant to limit the invention in any way. In preferred embodiments, and as shown in FIG. 6, the delivery ports comprise a permeable bioerodible polymeric layer through which the pharmaceutical active agent(s) must diffuse after implantation in order to provide therapeutic relief. If desired, the permeability of such layers is chosen such that the diffusion of the pharmaceutically active agents(s) through the layers is rate limiting.

The invention further relates to a method for treating a mammalian organism to obtain a desired local or systemic physiological or pharmacological effect. The method includes administering the implantable biodegradable drug delivery device to a mammalian organism and allowing the pharmaceutically active agent to diffuse from the device to produce the desired local or systemic effect. The term administering, as used herein, means positioning, inserting, injecting, implanting, anchoring, attaching or any other means for exposing the device to a mammalian organism, preferably a human. The route of administration depends on a variety of factors including type of response or treatment, type of agent, and preferred site of administration.

The devices in certain embodiments have applicability in providing a controlled and sustained release of agents effective in obtaining a desired local or systemic physiological or pharmacological effect relating at least to the following areas: treatment of cancerous primary tumors, (e.g., glioblastoma); inhibition of neovascularization, including ocular neovascularization; edema, including ocular edema; inflammation, including ocular inflammation; hormonal deficiencies such as diabetes; musculoskeletal disorders such as chronic pain; arthritis; rheumatic conditions; and dwarfism; and modification of the immune response such as in the prevention of transplant rejection and in cancer therapy. A wide variety of other disease states may also be prevented or treated using the drug delivery device of the present invention. Such disease states are known by those of ordinary skill in the art. For those not skilled in the art, reference may be made to Goodman and Gilman, The Pharmacological Basis of Therapeutics, 8th Ed., Pergamon Press, N.Y., 1990; and Remington's Pharmaceutical Sciences, 18th Ed., Mack Publishing Co., Easton, Pa., 1990; both of which are incorporated by reference herein.

The implantable biodegradable drug delivery devices of the invention are particularly suitable for treating ocular conditions such as glaucoma, proliferative vitreoretinopathy, macular edema, including diabetic macular edema, age-related macular degeneration, diabetic retinopathy, uveitis, ocular neovascularization, retinal vein occlusion, geographic atrophy, and ocular infection. The devices are also particularly suitable for use as an ocular device in treating mammalian organisms, both human and for veterinarian use, suffering from ocular histoplasmosis, wherein the device is surgically implanted within the vitreous of the eye.

In general, the implantable bioerodible drug delivery devices of the invention are designed to provide substantially zero-order release of one or more pharmaceutically active agents over a predetermined period of treatment. The predetermined period of treatment will vary depending on disease or disorder to be treated, the severity of the condition, and the desired duration of symptomatic relief. For example, in certain embodiments, the predetermined period lasts at least one month, two months, three months, four months, five months, six months or 12 months, and less than or equal to 48 months, 40 months, 36 months, 30 months, 24 months or eighteen months. In certain embodiments, the predetermined period is at least six months or at least twelve months. The invention recognizes that, in most cases, the more invasive the method of implantation is (e.g., surgical implantation), the more desirable it is to have a longer predetermined period for treatment. In this way, a patient can minimize his or her exposure to the trauma associated with the implantation process. In some embodiments, however, the predetermined period of treatment is relatively short (e.g., about three days, less than one week, about one week, about two weeks, or about three weeks). In some embodiments, the predetermined time is in the range of one to 30 days, one day to 180 days, six months to twelve months, or one year to three years.

The invention contemplates different methods for achieving the desired predetermined period of treatment. For example, the duration of the predetermined period of treatment can be adjusted by adjusting the physical length of the sustained release device, assuming that the sustained release device in question doses at a rate that is proportional to the area of the drug core exposed to the patient's bodily fluids. The duration of the predetermined period of treatment also may be adjusted by appropriate choice of a bioerodible polymer that is to be mixed with the pharmaceutically active agent in the drug core. As a non-limiting example, when the bioerodible polymer is polyvinyl alcohol, the polyvinyl alcohol may be heat treated to control or adjust the release rate of the pharmaceutically active agent(s). Typically, the heat treatment is performed after the pharmaceutically active agent is combined with the polyvinyl alcohol, in order to form a designed matrix and/or a diffusion port coating. However, the invention also recognizes that, in some instances, the drug core can be fully formed after heat treatment, so that the polyvinyl alcohol coating membrane can be processed at higher temperature to increase the polyvinyl alcohol crystallinity in order to further reduce the membrane permeability.

The above description of how to make the devices of the present invention is merely illustrative and should not be considered as limiting the scope of the invention in any way, as various compositions are well known by those skilled in the art. In particular, the methods of making the device depends on the identity of the active agent and polymers selected. Given the active agent and the composition of polymers that comprise the outer member and its delivery port(s), one skilled in the art could easily make the devices of the present invention using conventional coating techniques.

The method for treating a mammalian organism to obtain a desired local or systemic physiological or pharmacological effect includes administering the sustained release drug delivery device of the present invention to the mammalian organism and allowing the agent to pass through the device to come in direct contact with the mammalian organism.

The drug delivery system of the present invention may be administered to a mammalian organism via any route of administration known in the art. Such routes of administration include intraocular, oral, subcutaneous, intramuscular, intraperitoneal, intravitreal, intracameral, intranasal, dermal, into the brain, including intracranial and intradural, into the joints, including ankles, knees, hips, shoulders, elbows, wrists, directly into tumors, and the like. In addition, one or more of the devices may be administered at one time, or more than one agent may be included in the inner core or reservoir, or more than one reservoir may be provided in a single device.

The drug delivery system of the present invention is particularly suitable for direct implantation or injection into the vitreous of the eye and for application to an intraocular lens.

These methods of administration and technique for their preparation are well known by those of ordinary skill in the art. Techniques for their preparation are set forth in Remington's Pharmaceutical Sciences.

The drug delivery system may be administered for a sufficient period of time and under conditions to allow treatment of the disease state of concern.

For localized drug delivery, the devices may be surgically implanted at or near the site of action. This is the case for devices of the present invention used in treating ocular conditions, primary tumors, rheumatic and arthritic conditions, and chronic pain.

For systemic relief, the devices may be implanted subcutaneously, intramuscularly, intraarterially, intrathecally, or intraperitoneally. This is the case when devices are to give sustained systemic levels and avoid premature metabolism. In addition, such devices may be administered orally.

In one embodiment of the invention, an ocular device containing fluocinolone acetonide as the effective agent in a therapeutically effective amount to reduce or prevent ocular neovascularization may be prepared. Such devices may be used to effectively combat and inhibit undesirable ocular neovascularization, edema, or inflammation when surgically implanted into the vitreous of the eye. The preferred amount of fluocinolone acetonide used in these devices ranges from about 0.01 mg to about 40 mg. More preferably, such devices contain from about 0.1 mg to about 6 mg of fluocinolone acetonide. These preferred ranges may provide sustained release of the fluocinolone acetonide for a period of from several hours to over five years.

When such devices are prepared for implantation within the vitreous of the eye, it is preferred that the device does not exceed about 7 millimeters in any direction, so that the device can be inserted through a less than 7 millimeter incision. Thus, the cylindrical devices illustrated in the figures would preferably not exceed 7 millimeters in height or 3 millimeters in diameter. The preferred dimensions of the drug core are 3.5 mm L×0.37 mm Ø. The preferred thickness of bioerodible outer member ranges from 0.01 mm and about 1.0 mm. The preferred thickness of the permeable bioerodible polymer layers used to fabricate delivery ports ranges between about 0.01 mm and about 1.0 mm. The preferred thickness of the wall of outer layer ranges between about 0.01 mm and 1.0 mm.

EXAMPLES

Example 1

Fabrication of a Device for Treating Age-Related Macular Degeneration Using Tyrosine Kinase Inhibitors This example studies the release kinetics of an implantable bioerodible drug delivery device according to one embodiment of the invention. The implantable bioerodible drug delivery device used in this study was fabricated by grinding 250 mg of sunitinib, a tyrosine kinase inhibitor, to fine particles using a mortar and pestle. A volume of 250 µl of a 10% polyvinyl alcohol solution was added to the fine particles with additional mixing to form a composition with a consistency of a granulate/paste. The resulting granulate/paste was transferred into a 1.0 ml injector and extruded through a dispensing tip with a 0.013" ID to form a tubular drug core comprising the tyrosine kinase inhibitor and bioerodible polymer (polyvinyl alcohol). The extrudate was air-dried overnight.

The dried extrudate was heat-treated at 120° C. for two hours and then dip-coated in a 5% polyvinyl alcohol (PVA) solution. The dip-coated extrudate was subsequently air-dried for 30 min. at 25° C. The PVA-coated extrudate was then coated with 7% PLGA (75:25) solution in acetone and air-dried for 30 min. at 25° C. The cycle of coating in a 7% PLGA (75:25) solution and then air-drying for 30 min. at 25° C. was repeated two more times. The coated extrudate was then heated at 60° C. for 60 min.

Figure 7:
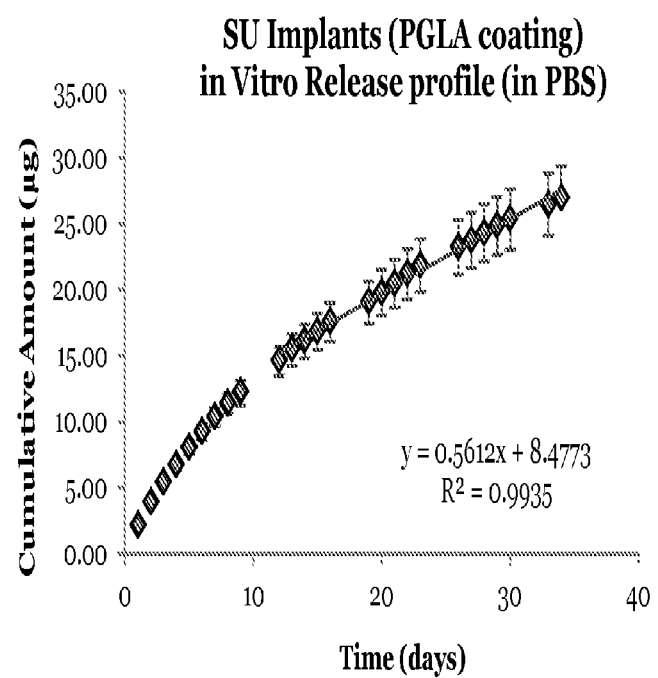
FIG. 7: A plot showing the release profile of a device according to one embodiment of the invention.

To study the release profile of the coated extrudate, the extrudate was cut into pieces, with each piece having a length of about 3.5 mm. One of the pieces was placed in 1.0 ml volume of phosphate buffered saline (PBS) that was maintained at 37° C. via immersion in a water bath. FIG. 7 shows a plot of the release profile of the device as a function of time. Aside from an initial non-linear induction period during the first ten days of the experiment, the plot shows that the cumulative amount of the API released grows essentially linearly ($R^2=0.9935$) with time from about day 12 to about day 35. This linear behavior is characteristic of a constant rate of release over the same time period. Thus, the plot in FIG. 7 shows that the device fabricated in this example is capable of achieving substantially zero order release kinetics.

Example 2

Description of Erodible Durasert Implants with PLGA Micro-Tubes

An implantable bioerodible device in accordance with one embodiment of the invention was fabricated in the following manner. A 950 mg sample of fluocinolone acetonide (FA) was combined with 950 µl of a 10% polyvinyl alcohol to form a granulate/paste composition. The granulate/paste composition was transferred into a syringe and extruded into two different types of poly(lactic-co-glycolic acid) (PLGA) micro-tubes. The first type of tube had a lactic acid/glycolic acid molar ratio of 85:15 (i.e., L85:G15), while the second type of tube had a lactic acid/glycolic acid molar ratio of 82:18 (L82:G18). After air drying, the filled tubes were cut into 3.0 or 3.5 mm long pieces, and both ends of the each piece were coated with a 10% PVA and air dried at 25° C. for 30 min. The cycle of coating with PVA solution and then air-drying for 30 min at 25° C. was repeated two more times. The implants were subjected to heat-treatment at 105° C. for 2 hours.

Example 3

Release Profile of PLGA Micro-Tube

An implantable bioerodible micro-tube device in accordance with one embodiment of the invention was fabricated with the designing principle that the pharmaceutically active agent should be released at a steady and controlled rate from the micro-tube and only from the release ports on both ends of the micro-tube, with the shell of the tube not permeable to the pharmaceutically active agent in the drug core. In addition, the micro-tube was designed to maintain its structural and mechanic integrity until the loaded pharmaceutically active agent is completely released.

This implantable bioerodible micro-tube device had an inner diameter of 0.20 mm, a wall thickness of about 0.075 mm, and length of 3.5 mm. The outer shell of the micro-tube was made of a PLGA polymer (lactic acid/glycolic acid molar ratio 85:15) micro-tube, and the device was fabricated by extruding a granulated fluocinolone acetonide/polyvinyl alcohol (PVA) composition into the PLGA micro-tube. Both ends of the implant were coated with a 10% aqueous PVA solution, air dried and heated treated at 105° C. for two hours.

Figure 8:
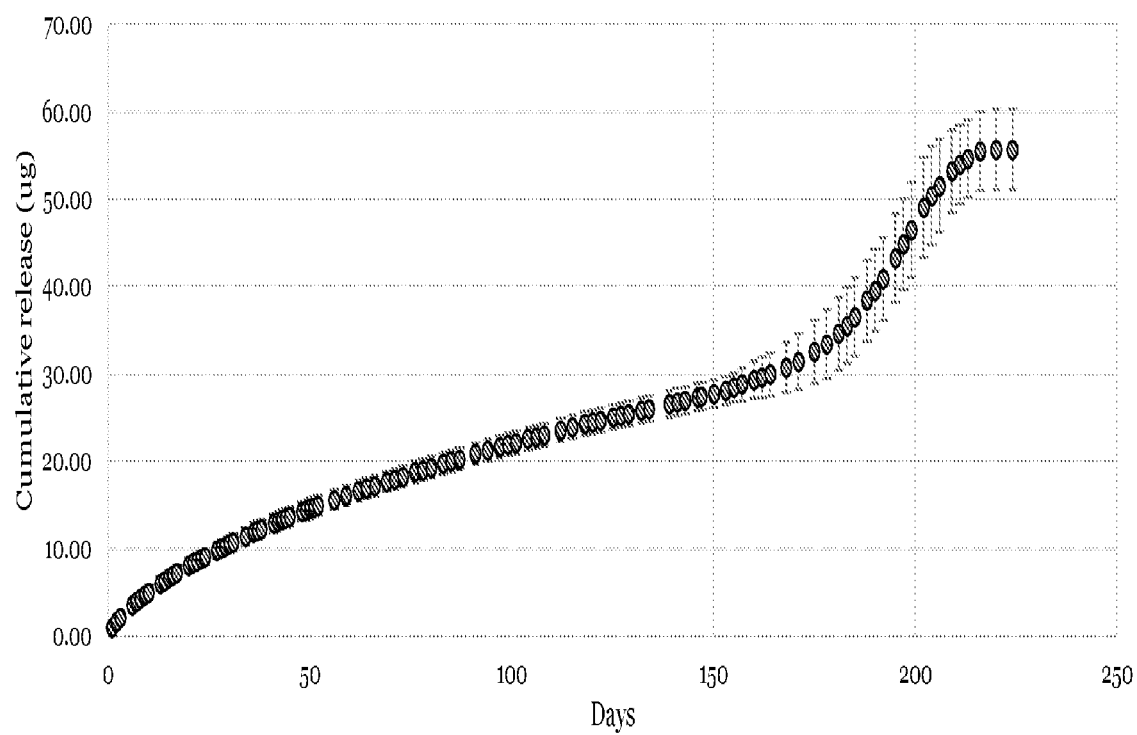
FIG. 8: A plot showing the release profile of a device according to one embodiment of the invention.

An in-vitro release experiment was performed by immersing the device in a release medium, which was phosphate buffered saline (PBS) maintained at 37° C. in a water bath. The PBS release medium was removed periodically for analysis and replaced with fresh PBS. The release profile that was obtained (FIG. 8) was essentially linear for about 160 days, which suggests that the drug was only released from the release ports on both ends of the device during this time. After about 160 days, the release rate of the pharmaceutically active agent increased, indicating that the micro-tube itself had degraded sufficiently to allow the pharmaceutically active agent to permeate the PLGA walls of the micro-tube. The release profile of this device indicates that it is suitable for controlled sustained-release of a pharmaceutically agent for up to about 160 days. An advantage of using this implantable bioerodible device to treat ocular disorders is that the device dissolves relatively rapidly after it has delivered its pharmaceutically active agent. Thus, upon subsequent injection of another implantable bioerodible device of the same type to continue treatment of the ocular disorder, there are at most only two devices within the patient's eye at any given time.

While the above described embodiments of the invention are described in terms of preferred ranges of the amount of pharmaceutically active agent, and preferred thicknesses of the bioerodible polymeric layers, these preferences are by no means meant to limit the invention. As would be readily understood by one skilled in the art, the preferred amounts, materials and dimensions depend on the method of administration, the effective agent used, the polymers used, the desired release rate and the like. Likewise, actual release rates and release duration depend on a variety of factors in addition to the above, such as the disease state being treated, the age and condition of the patient, the route of administration, as well as other factors which would be readily apparent to those skilled in the art. All of the foregoing U.S. Patents and other publications are expressly incorporated by reference herein in each of their entireties.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be, within the full range of equivalence of the following claims.

What is claimed is:

1. A method of treating an eye disease or disorder in a patient, the method comprising
   identifying an area of a patient's eye in need of treatment;
   implanting a bioerodible drug delivery device in sufficient proximity to the area in need of treatment to provide therapeutic relief, wherein the bioerodible drug delivery device comprises
      a bioerodible drug core comprising a pharmaceutically active agent and polyvinyl alcohol,
      a bioerodible outer member that substantially surrounds the drug core, wherein the bioerodible outer member comprises poly(lactic-co-glycolic) acid (PLGA) where lactic acid/glycolic acid is present in a molar ratio ranging from and including 82:18 to 85:15; and
      at least one delivery port that is permeable to the pharmaceutically active agent;
   wherein the device is configured to be injected into the vitreous of the patient's eye; and
   wherein the device is configured to provide a substantially constant dosing rate of the pharmaceutically active agent for at least one month.

2. The method of claim 1, wherein the pharmaceutically active agent is selected from the group consisting of anesthetics, anti-cancer agents, anti-fungal agents, anti-viral agents, cell transport/mobility impeding agents, anti-glaucoma agents, immunological response modifiers, peptides, proteins, steroidal compounds, corticosteroids, antibacterial agents, neuro-protectants, anti-inflammatory agents, anti-allergenic agents, anti-cholinesterases, miotics, and mydriatics.

3. The method of claim 1, wherein the bioerodible outer member is tubular.

4. The method of claim 3, wherein each end of the tubular bioerodible outer member comprises a delivery port.

5. The method of claim 1, wherein the device is configured to provide a substantially constant dosing rate of the pharmaceutically active agent for one month to six months.

6. The method of claim 1, wherein the device is configured to provide a substantially constant dosing rate of the pharmaceutically active agent for six months to one year.

7. The method of claim 1, wherein the device is configured to provide a substantially constant dosing rate of the pharmaceutically active agent for one to three years.

8. The method of claim 1, wherein the pharmaceutically active agent is a corticosteroid.

9. The method of claim 1, wherein the device is configured to provide a substantially constant dosing rate of the pharmaceutically active agent for at least two months.

10. The method of claim 1, wherein the device is designed to fit through a needle with a gauge of 25 or larger.

11. The method of claim 4, wherein at least one delivery port has a polymeric cap.

12. The method of claim 4, wherein at least one delivery port has a polyvinyl alcohol cap.

13. The method of claim 1, wherein the polyvinyl alcohol constitutes about 1 to about 20% w/w of the drug core.

14. The method of claim 1, wherein the drug core was manufactured using a solution of about 5 to about 15% w/w polyvinyl alcohol.

15. The method of claim 1, wherein the drug core was heat treated during manufacturing.

16. The method of claim 1, wherein the device was heat treated during manufacturing.

17. The method of claim 1, wherein the eye disease or disorder is selected from the group consisting of glaucoma, proliferative vitreoretinopathy, macular edema, diabetic macular edema, age-related macular degeneration, diabetic retinopathy, uveitis, ocular neovascularization, retinal vein occlusion, geographic atrophy, and ocular infection.

* * * * *